(12) United States Patent
Moosmann et al.

(10) Patent No.: US 8,232,243 B2
(45) Date of Patent: Jul. 31, 2012

(54) TYROSINE- AND TRYPTOPHAN-CONTAINING PEPTIDES AS ANTIOXIDANTS

(75) Inventors: Bernd Moosmann, Munich (DE); Christian Behl, Munich (DE)

(73) Assignee: Max-Planck-Gesellschaft zur Forderung der Wissenschaften E.V., München (DE)

( * ) Notice: Subject to any disclaimer, the term of this patent is extended or adjusted under 35 U.S.C. 154(b) by 850 days.

(21) Appl. No.: 10/148,557

(22) PCT Filed: Dec. 4, 2000

(86) PCT No.: PCT/EP00/12177
§ 371 (c)(1), (2), (4) Date: Jul. 9, 2002

(87) PCT Pub. No.: WO01/39791
PCT Pub. Date: Jun. 7, 2001

(65) Prior Publication Data
US 2003/0054976 A1    Mar. 20, 2003

(30) Foreign Application Priority Data

Dec. 2, 1999 (DE) ................................. 199 58 121

(51) Int. Cl.
*A61K 38/17* (2006.01)
(52) U.S. Cl. ........................................ 514/1.9; 514/16.6
(58) Field of Classification Search .................... 514/19, 514/16, 15, 14; 530/330, 328, 326
See application file for complete search history.

(56) References Cited

U.S. PATENT DOCUMENTS

| | | | |
|---|---|---|---|
| 5,283,236 A | 2/1994 | Chiou | |
| 5,736,509 A * | 4/1998 | Balaji et al. | 514/9 |
| 5,760,087 A | 6/1998 | Patoiseau et al. | |
| 5,807,830 A | 9/1998 | Morozov et al. | |
| 5,961,959 A | 10/1999 | Gers-Barlag et al. | |
| 6,019,967 A * | 2/2000 | Breton et al. | 424/130.1 |

FOREIGN PATENT DOCUMENTS

| | | |
|---|---|---|
| DE | 29 32 923 A | 2/1981 |
| DE | 38 36 849 A | 6/1989 |
| EP | 0 173 181 A1 | 3/1986 |
| EP | 0 871 611 B1 | 10/1998 |
| GB | 536406 | 5/1941 |
| JP | 0058065785 | 4/1983 |
| WO | WO 90/06102 | 6/1990 |
| WO | WO 91 12267 A | 8/1991 |
| WO | WO-92/13549 | 8/1992 |
| WO | WO-99/02163 | 1/1999 |

OTHER PUBLICATIONS

Sigma. Designing Custom Peptides. http://www.sigmaaldrich.com, 2004.*
Berendsen "A Glimpse of the Holy Grail?" Science, 1998, vol. 282, pp. 642-643.*
Voet and Voet, Biochemistry, 2nd edition, 1995, pp. 235-241.*
Smilek, Proc. Natl. Acad. Sci. USA, 1991, vol. 88, pp. 9633-9637.*
Smilek et al., Proc. Natl. Acad. Sci. USA 1991, #88, pp. 9633-9637.*
Smilek et al., Proc. Natl. Acad. Sci. USA, 1991, vol. 88, pp. 9633-9637.*
Decrease in Peptide Methionine Sulfoxide Reductase in Alzheimer's Disease Brain, Gabbita. Journal of Neurochemistry. vol. 73, Oct. 1999.
Separation of Tryptophan Pyrrolooxygehase into three molecular forms, Camorett-Mercado, et al. Eur. J. Biochem. (1986).
Characterization of a Multi-lipopeptides mixture used as an HIV-1 vaccine candidate, Klinguer, et al. Vaccine 18 (1999).
Russian Chem. Abstr. 126:325789 Kovalenko et al, Asymmetry of peripheral effects of unilateral intranasal oxytocin injection in white male rats, Doklady Akademii Nauk (1995), 342(2), 269-272, Issn: 0869-5652.
Moosman, et al "Cytoprotective antioxidant function . . . Proteins.", European Journal of Biochemistry, vol. 267, No. 18, Sep. 2000, pp. 5687-5692.
Structural analysis of Antioxidative peptides from Soybean, Chen, et al. Department of Applied Biological Chemistry, Faculty of Agriculture, (1995 (American Chemical Society.
Antioxidant Activity of Designed Peptides Based on the Antioxidative Peptide Isolated from Digests of a soybean Protein, Chen, Department of Applied Biological Chemistry, (1996) American Chemical Society.
Abstract of JP 6345797 A (Dec. 1994).
Thomas Sr Stocker R. "Antioxidant activities and redox regulation of interferon-gamma-induced tryptophan metabolism in human monocytes and macrophages", Adv. Exp. Med Biol. 1999; 467:541-52.
Kawashima, Antioxidant Properties of Branched-chain Amino Acid Derivative, Chem. Pharm. Bull., (1979), vol. 27. No. 8, pp. 1912-1914.

* cited by examiner

*Primary Examiner* — Christopher R. Tate
*Assistant Examiner* — Roy Teller
(74) *Attorney, Agent, or Firm* — Fulbright & Jaworski L.L.P.

(57) ABSTRACT

The invention relates to the use of tryptophan-containing, in particular tryptophan- and tyrosine-containing, peptides as antioxidants. The compounds can be used for the therapy or prophylaxis of syndromes and disorders associated with unwanted oxidative processes in the extracellular space.

10 Claims, 14 Drawing Sheets

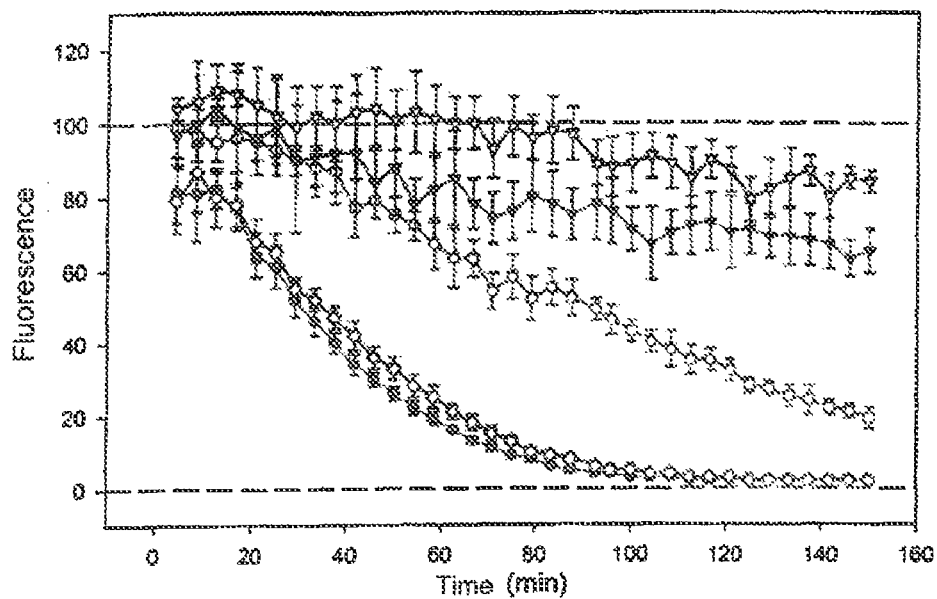
Figure 1A. GnRH (gonadotropin-releasing hormone) (human)

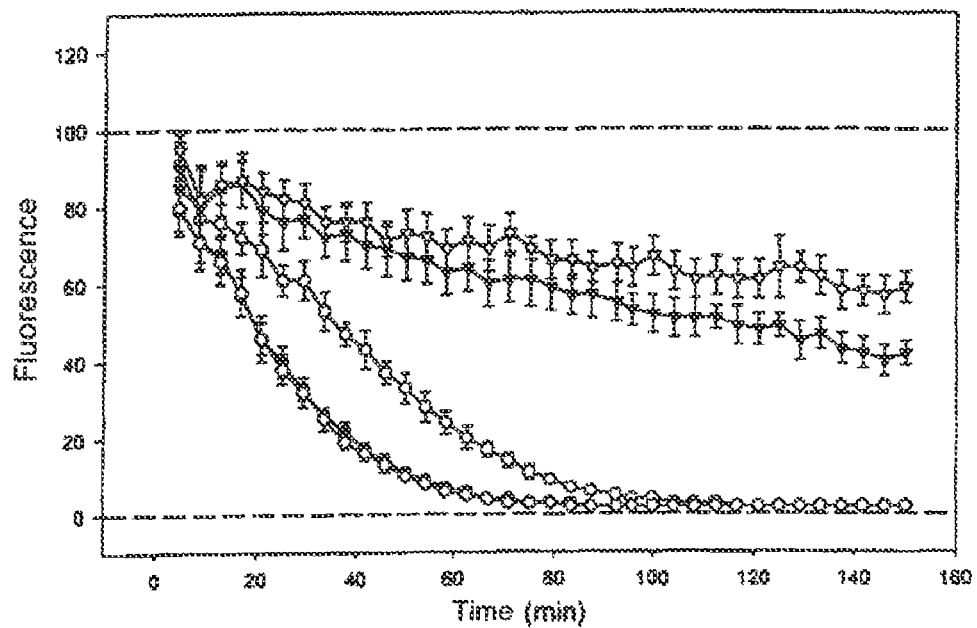
Figure 1A. (continued) WGGGY

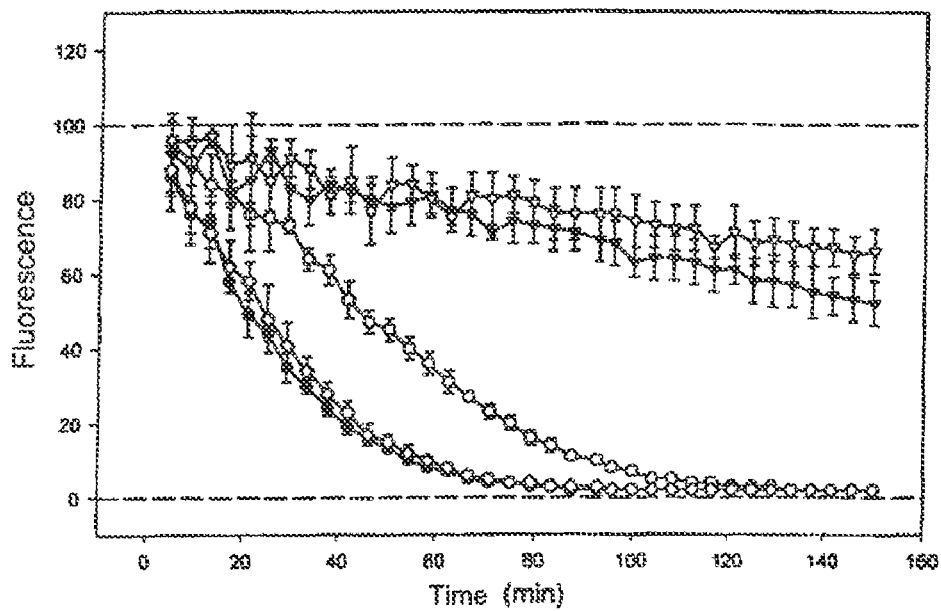
Figure 1A. (continued) WW

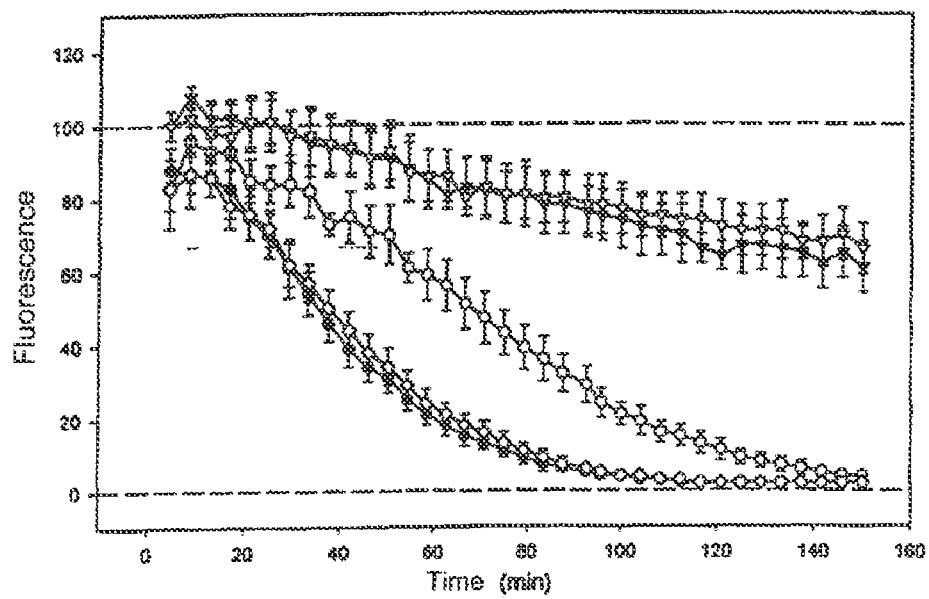
Figure 1A. (continued) WY

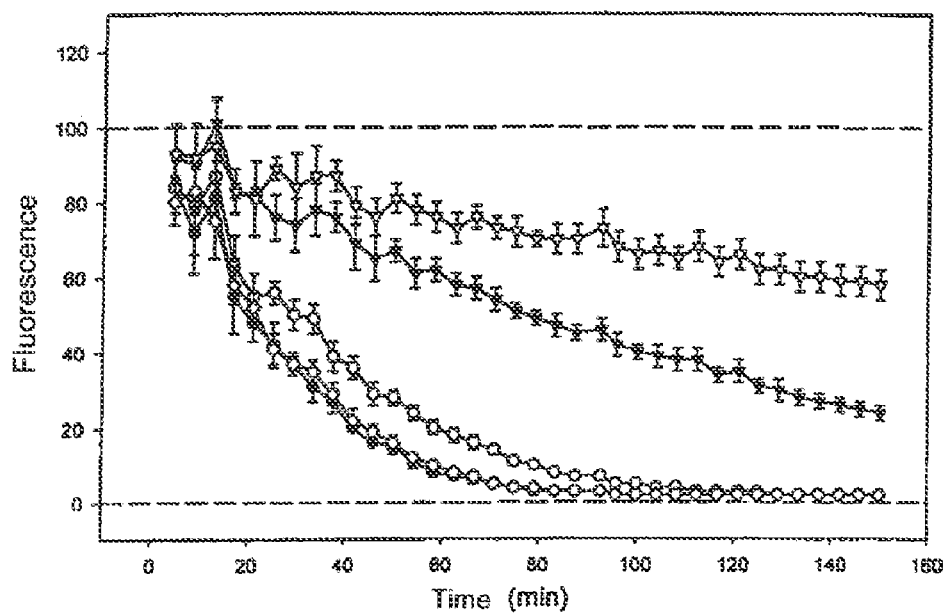
Figure 1A. (continued) YY

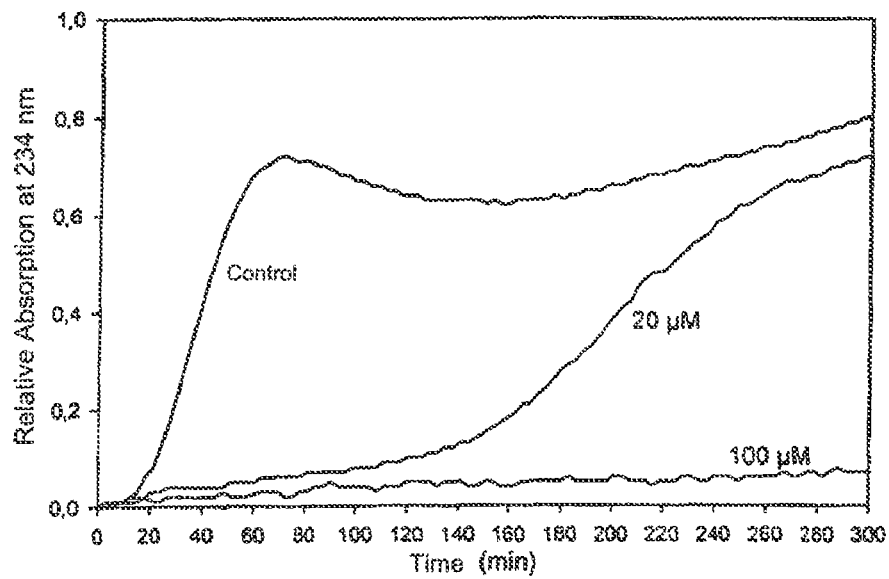
Figure 1B. GnRH (gonadotropin-releasing hormone) (human)

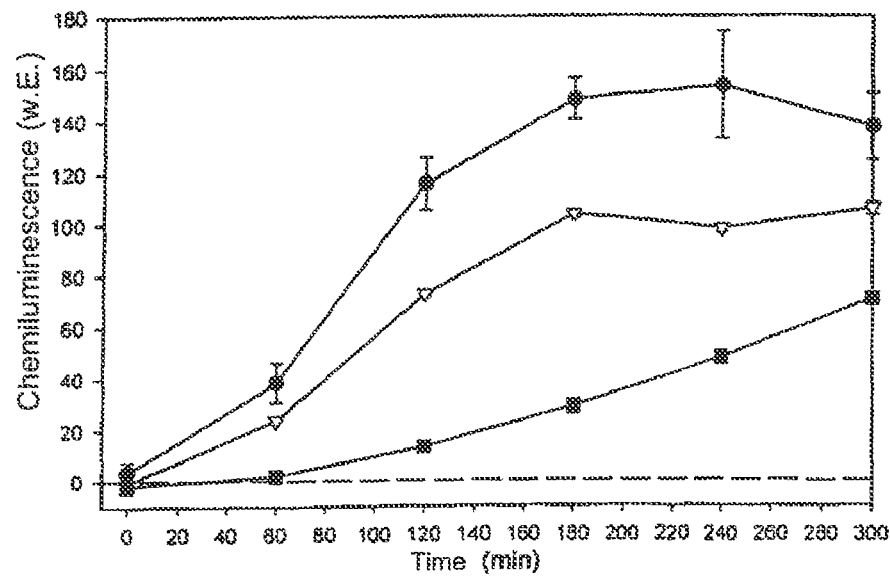
Figure 1C. GnRH (gonadotropin-releasing hormone) (human)

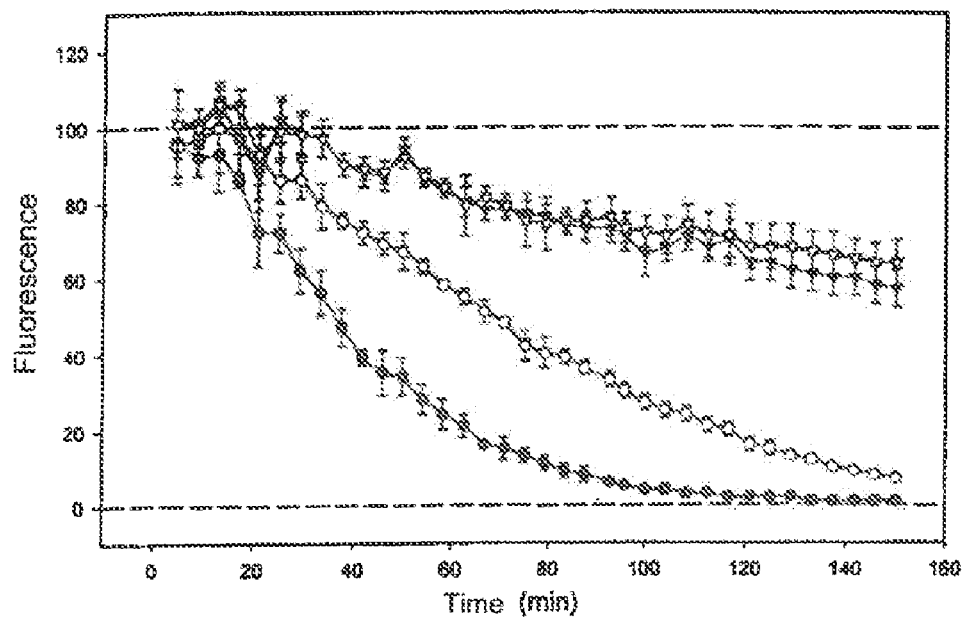
Figure 2. GnRH 3-10

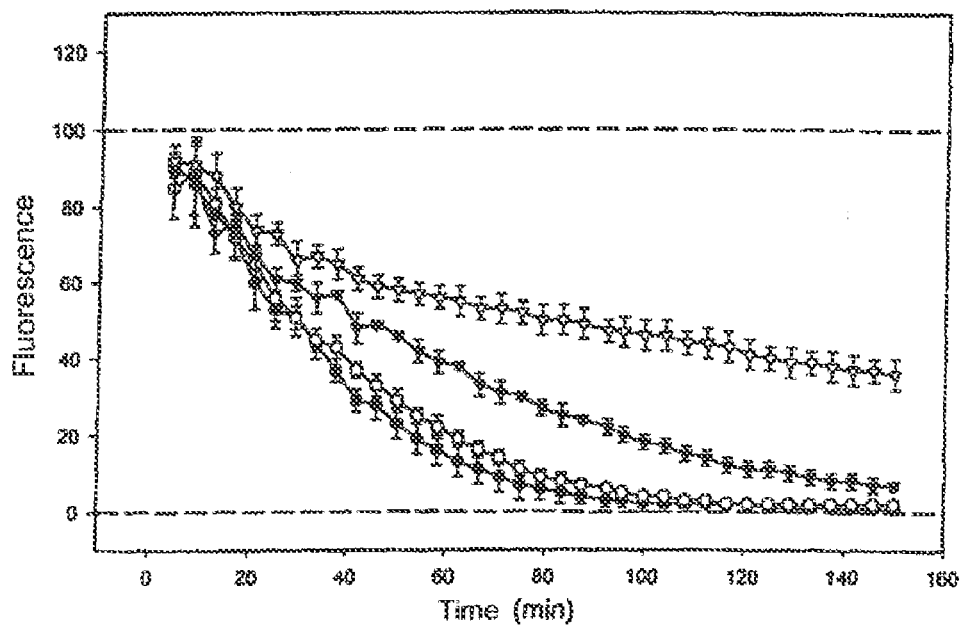
Figure 2. (continued) GnRH 4-10

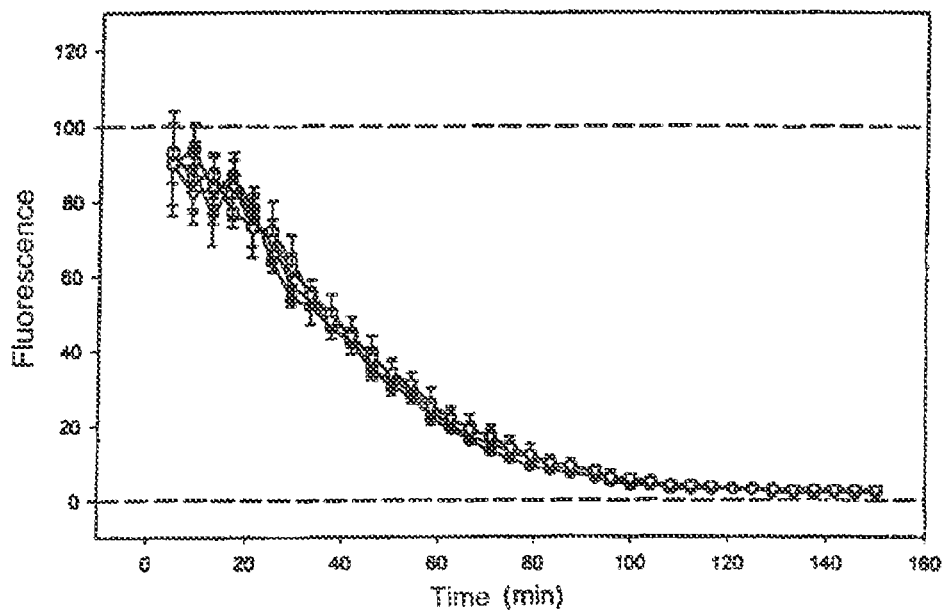
Figure 2. (continued) GnRH 7-10

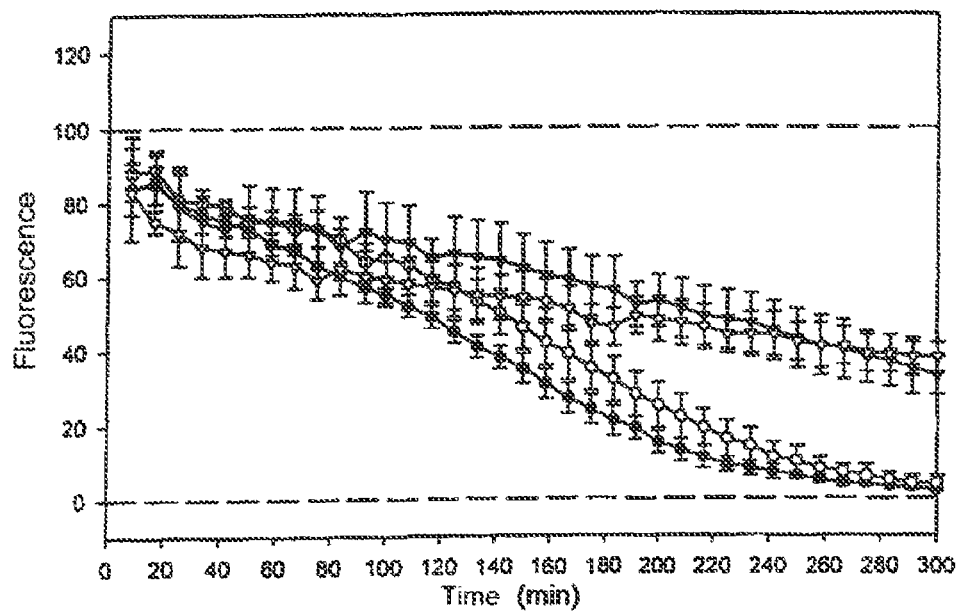
Figure 3. Estradiol

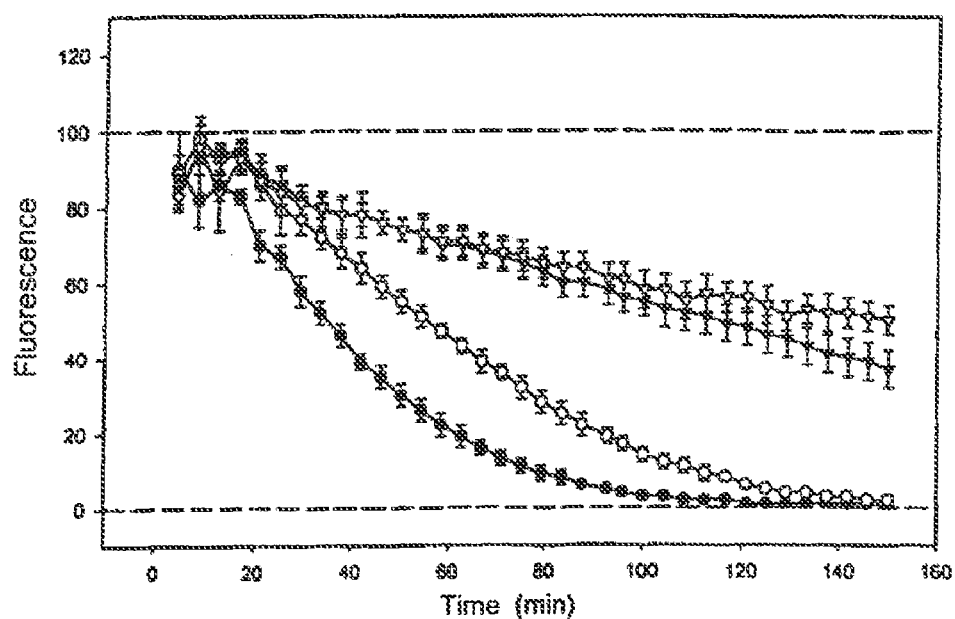
Figure 3. (continued) Melatonin

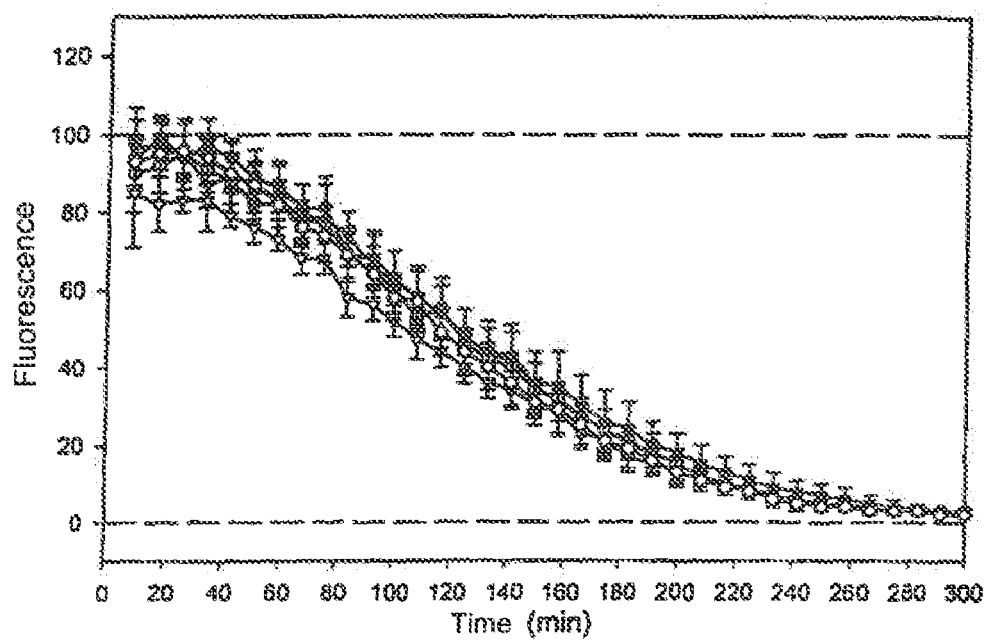
Figure 3. (continued) Probucol

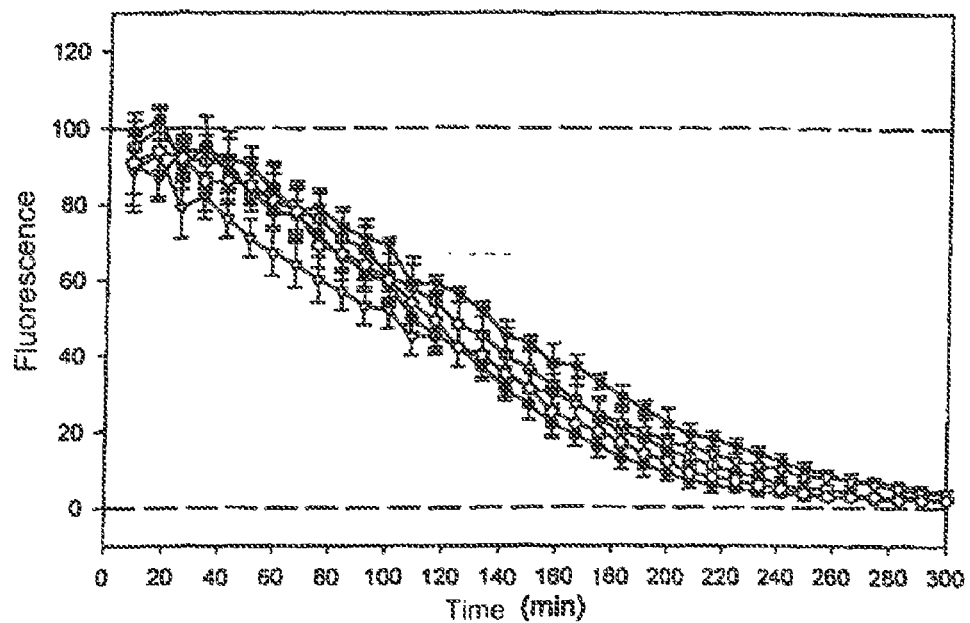
Figure 3. (continued) Tocopherol

SEQUENCE LISTING

<160> NUMBER OF SEQ ID NOS: 9

<210> SEQ ID NO 1
<211> LENGTH: 10
<212> TYPE: PRT
<213> ORGANISM: Homo Sapiens
<220> FEATURE:

<400> SEQUENCE: 1

Glu His Trp Ser Tyr Gly Leu Arg Pro Gly
1               5                   10

<210> SEQ ID NO 2
<211> LENGTH: 10
<212> TYPE: PRT
<213> ORGANISM: Oncorhynchus tshawytscha
<220> FEATURE:

<400> SEQUENCE: 2

Glu His Trp Ser Tyr Gly Trp Leu Pro Gly
1               5                   10

<210> SEQ ID NO 3
<211> LENGTH: 10
<212> TYPE: PRT
<213> ORGANISM: Petromyzon marinus
<220> FEATURE:

<400> SEQUENCE: 3

Glu His Trp Ser His Asp Trp Lys Pro Gly
1               5                   10

<210> SEQ ID NO 4
<211> LENGTH: 4
<212> TYPE: PRT
<213> ORGANISM: Phyllomedusa bicolor
<220> FEATURE:

<400> SEQUENCE: 4

Ala Pro Gly Tyr
1

<210> SEQ ID NO 5
<211> LENGTH: 4
<212> TYPE: PRT
<213> ORGANISM: Artificial sequence
<220> FEATURE:
<223> OTHER INFORMATION: A synthetic peptide which functions as an
      antioxidant

<400> SEQUENCE: 5

Trp Gly Gly Tyr
1

<210> SEQ ID NO 6
<211> LENGTH: 5
<212> TYPE: PRT
<213> ORGANISM: Artificial sequence
<220> FEATURE:
<223> OTHER INFORMATION: A synthetic peptide which functions as an
      antioxidant

<400> SEQUENCE: 6

Trp Gly Gly Gly Tyr
1               5

```
<210> SEQ ID NO 7
<211> LENGTH: 8
<212> TYPE: PRT
<213> ORGANISM: Homo sapiens
<220> FEATURE:

<400> SEQUENCE: 7

Trp Ser Tyr Gly Leu Arg Pro Gly
1               5

<210> SEQ ID NO 8
<211> LENGTH: 7
<212> TYPE: PRT
<213> ORGANISM: Homo sapiens
<220> FEATURE:

<400> SEQUENCE: 8

Ser Tyr Gly Leu Arg Pro Gly
1               5

<210> SEQ ID NO 9
<211> LENGTH: 4
<212> TYPE: PRT
<213> ORGANISM: Homo sapiens
<220> FEATURE:

<400> SEQUENCE: 9

Leu Arg Pro Gly
1
```

TYROSINE- AND TRYPTOPHAN-CONTAINING PEPTIDES AS ANTIOXIDANTS

The invention relates to the use of tryptophan-containing, in particular tryptophan- and tyrosine-containing, peptides as antioxidants. The compounds can be used for the therapy or prophylaxis of syndromes or disorders associated with unwanted oxidative processes in the extracellular space.

Many disorders are associated with increased oxidative stress. This may lead to various cellular reactions such as, for example, differentiation, apoptosis, necrosis or oxidative cytolysis (Irani et al., Science 275 (1997), 1649; Burdon, Free Radic. Biol. Med. 18 (1995), 775; Anderson et al., Med. Hypotheses 52 (1999), 451; Hampton and Orrenius, Toxicol. Lett. 102-103 (1998), 355; Kowaltowski and Vercesi, Free Radic. Biol. Med. 26 (1999), 463; Beal, Ann. Neurol. 38 (1995), 357).

Oxidative processes may also influence the structure and functionality of the extracellular space, which may lead to disadvantageous biochemical and physiological changes. Examples are the oxidation of low density lipoprotein (LDL), which is causally involved in artherosclerotic processes (Heinecke, J. Clin. Invest. 104 (1999), 135; Parthasarathy, Annu. Rev. Med. 43 (1992), 219), the changes in the aggregation behavior of lens proteins, which lead to cataracts (Christen, Proc. Assoc. Am. Physicians 111 (1999), 16; Taylor and Nowell, Adv. Pharmacol. 38 (1997), 515) or the oxidative crosslinking of collagen which is found in diabetes, arthritis or aging processes (Bailey et al., Mech. Ageing Dev. 106 (1998), 1; Beckmann and Ames, Physiol. Rev. 78 (1998), 547). Another additional factor is that the number of known antioxidant systems in the extracellular space is less than inside the cell (van der Vlies et al., Am. J. Physiol. 276 (1999), L289; Frei et al., Proc. Natl. Acad. Sci. USA 85 (1988), 9748; Mimic-Oka et al., Clin. Nephrol. 51 (1999), 233; Cross et al., Environ. Health Perspect. 106 Suppl 5 (1998), 1241; Wilson, Can. J. Physiol. Pharmacol. 75 (1997), 1149; Grootveld et al., Free Radic. Res. 30 (1999), 351; Sies, Exp. Physiol. 82 (1997), 291).

There is thus a great need for substances which firstly have a strong effect as antioxidants in the extracellular space, and secondly are physiologically tolerated.

In the present investigations to the present invention, a new class of biochemical antioxidants in the extracellular space was identified. These are low molecular weight soluble peptides which comprise aromatic ring systems able to form stable free radicals, in particular tryptophan residues, preferably tryptophan residues and tyrosine residues. These peptides prevent or reduce the oxidation of physiologically important components of the extracellular space, e.g. dissolved proteins, fibrillar proteins, lipoprotein particles and membrane lipids. Since oxidation of these biological components occurs in a large number of degenerative disorders, the invention represents an important new finding in the medical sector.

The antioxidants of the invention can be prepared in large quantities in a chemically simple manner and at low cost, whereas known antioxidants with extracellular activity (e.g. ascorbate, tocopherol, ubiquinol) are either considerably more costly (tocopherol, ubiquinol) or less effective (ascorbate). The compounds of the invention are also considerably more stable than the known antioxidants because they are essentially stable to atmospheric oxygen but show a high reactivity for oxygen-based free radicals which damage tissues. In addition, the compounds are amphiphilic, i.e. they are water-soluble, but can also be incorporated in a technically simple manner, e.g. by ultrasonic treatment, into lipophilic formulations, e.g. liposomes. Yet a further advantage is that the compounds of the invention do not penetrate intact cells, i.e. even with low dosages they accumulate in the extracellular space. It is moreover possible to employ natural compounds consisting entirely of amino acids which occur endogenously and which do not display metabolically accumulative or toxic effects. Finally, the compounds show only a small tendency to plasma protein binding, so that the freely diffusible, active concentrations are higher.

One aspect of the invention is thus the use of compounds which comprise at least one tryptophan residue or/and an analogous aromatic residue or/and at least two tyrosine residues or/and analogous aromatic residues, and have a molecular mass of up to 2 500 Da, for the preparation of an agent for inhibiting oxidative processes. The compounds are particularly suitable for the therapy or prophylaxis of disorders associated with oxidative processes in the extra-cellular space, for example of degenerative disorders such as, for example, artherosclerosis, diabetes, cataracts, arthritis and aging processes in joints or skin. The compounds are particularly preferably employed in skin creams to retard aging of the skin, in particular before, during, or after UV exposure, and as prophylactic or medicament for arthritic or rheumatic oxidative processes, and for artherosclerosis.

The compounds are able to inhibit the start or progression of oxidative processes on physiological components of the extracellular space such as, for example, soluble proteins, fibrillar proteins, e.g. collagen, glycoproteins, proteoglycans, lipoproteins, e.g. lipoprotein particles such as LDL, and membrane lipids. Preference is given to the use of low molecular weight peptides with amphiphilic properties, i.e. compounds which are, on the one hand, soluble in water and, on the other hand, have an affinity for nonpolar organic residues. In one embodiment, the peptides comprise at least one tryptophan residue or an analogous aromatic residue and, where appropriate, additionally at least one tyrosine residue or an analogous aromatic residue. In another embodiment, the peptides comprise at least two tyrosine residues or analogous aromatic residues and, where appropriate, additionally at least one tryptophan residue or an analogous aromatic residue. Examples of suitable analogous residues are, in particular, aromatic amino acid residues with a phenol- or a tryptophan-analogous indole ring system, such as, for example, an alkyloxyphenol or alkyloxyindole ring, in particular a methoxyphenol or methoxyindole ring. The amino acid residues with antioxidant activity may be in the L or/and in the D conformation. The L conformation is preferred.

In one embodiment of the invention, the compounds are selected from peptides with a length of from 2 to 15, preferably 2 to 10 and particularly preferably 2 to 7, amino acids. Peptides in the sense of the present invention are essentially compounds composed of amino acids, in particular of α-amino carboxylic acids, e.g. of natural genetically encoded amino acids, but also of other amino acids, where the amino acid residues are linked together by peptide bonds. The peptides may additionally have, where appropriate, N- or/and C-terminal modifications, e.g. an N-terminal acylation or a C-terminal esterification or amidation or a cyclic structure.

The compounds preferably comprise at least two tyrosine, tryptophan or/and analogous aromatic residues, e.g. at least two tyrosine residues, at least one tryptophan residue and one tyrosine residue or at least two tryptophan residues. It has emerged in this connection that a spatial proximity of these residues may be desirable, e.g. in the case of peptide compounds the residues with antioxidant activity are preferably either directly adjacent or separated by one or a maximum of two intermediate amino acid residues. It is further preferred for the compounds to comprise up to four of the residues with antioxidant activity. However, there are cases in which the compounds may also comprise a larger number of residues with antioxidant activity.

The investigations leading to the present invention were carried out on physiologically active peptide hormones with tryptophan residues, preferably tryptophan residues and tyrosine residues. It was found therein that the antioxidant effect is correlated not with other structural-specific physiological effects of these peptide hormones but only with the presence of tryptophan residues, in particular tryptophan residues and tyrosine residues. In order to avoid as far as possible unwanted physiological side effects during medical treatment with the compounds of the invention, therefore, the compounds of the invention, e.g. peptides, are selected such that they have essentially no structural-specific physiological effect, e.g. a hormonal effect.

Examples of secretory peptides with antioxidant activity are listed in the following table.

TABLE

| Peptide | Amino acid sequence |
| --- | --- |
| GnRH (gonadotrophin-releasing hormone) (human) | cyEHWSYGLRPG-amide (SEQ ID NO: 1) |
| GnRH (gonadotrophin-releasing hormone) (salmon) | cyEHWSYGWLPG-amide (SEQ ID NO: 2) |
| GnRH (gonadotrophin-releasing hormone) (lamprey) | cyEHWSHDWKPG-amide (SEQ ID NO: 3) |
| Dermorphin | $Y^D$-AFGY PS-amide (SEQ ID NO: 4) | cyE = cyclic glutamate
$X^D$ = D-amino acid

Besides these peptides, all truncated fragments thereof have activity as long as the tyrosine or tryptophan content thereof is not reduced.

Examples of synthetic peptides which are effective as antioxidants but which have no hormonal effect are WY, WGY, WGGY (SEQ ID NO: 5), WGGGY (SEQ ID NO: 6), WW, and YY.

Administration of the compounds depends on the nature and severity of the disorder to be treated and on the mode of administration. Administration preferably takes place in such a way that an active ingredient concentration in the range from 1 nM to 100 μm, in particular 2 nM to 20 μM, is present at the target site. Administration can be systemic, e.g. by intravascular injection, but especially by oral administration. On the other hand, however, administration may also be local, e.g. by intramuscular or subcutaneous injection, but especially by topical application.

In a particularly preferred embodiment of the invention, the substances with antioxidant activity are added to a sun cream formulation in order to prevent damage to the skin through exposure to UV. One aspect of the invention is thus also a sun cream formulation which, besides conventional ingredients, comprises an amount having antioxidant activity of peptides with at least one tryptophan residue or/and an analogous aromatic residue. The amount of the peptides with antioxidant activity in the sun cream formulation is preferably from 0.5 to 10% by weight.

The invention is to be illustrated further by the following figures and examples. These show:

FIG. 1 the antioxidant effect of tryptophan-containing, in particular tryptophan- and tyrosine-containing peptides in trapping peroxy free radicals (A), in preventing LDL oxidation (B) and in preventing peroxidation of brain lipids (C), and FIG. 2 the essential importance of tryptophan residues, in particular tryptophan and tyrosine residues, for the antioxidant effect of peptides, and FIG. 3 the antioxidant effect of comparative substances.

EXAMPLES

1.

The ability of peptides to protect the globular protein B-phycoerythrin from destruction by peroxy free radicals was tested. This was done by oxidizing B-phycoerythrin from Porphyrium cruentum (10 nM) in phosphate-buffered saline solution using 2,2'-azobis-2-methylpropionamidine (500 μM) at 37° C. as source of peroxy free radicals. Destruction of the protein was measured by observing the decrease in the protein fluorescence with increasing incubation time (flash fluorimetry, excitation window 340±50 nm, emission window 572±6 nm). The results of this experiment for the secretory peptides GnRH (human) and for the synthetic peptides WY, WGGGY, WW and YY are shown in FIG. 1A. The meanings in the individual diagrams are • the control and ◇ a concentration of 20 nM, ○ 200 nM, ▼ 2 μM and ∇ 20 μM of the particular peptide (quadruplicate determinations). Analogous results were obtained with the secretory peptides GnRH (salmon), GnRH (lamprey) and dermorphin and for the synthetic peptides WGY and WGGY.

In a further test, the ability of the peptides to protect LDL from copper-catalyzed oxidation was tested. This was done by incubating fresh human LDL (0.1 mg/ml protein) with 10 μM $CuSO_4$ at 37° C. The reaction products of the LDL decomposition (conjugated dienes) were measured by photometry at 234 nm as described by Moosmann and Behl (Proc. Natl. Acad. Sci. USA 96 (1999), 8867). The results for the secretory peptide GnRH (human) are shown in FIG. 1B. The three curves show the control, a concentration of 20 μM and a concentration of 100 μM of the particular peptide (duplicate determinations).

Secretory peptides are able to protect brain membranes from oxidative damage by ascorbate. This was done by oxidizing native rat brain membranes (0.5 mg/ml protein) by adding 50 μM ascorbate at 37° C. Single-photon measurement of the chemiluminescence (as measure of peroxidation reactions occurring) was measured for quantitative determination of the lipid peroxidation as described by Moosmann and Behl (supra). The results for GnRH (human) are shown in FIG. 1C. • means the control and ◇ a concentration of 20 μM and ■ a concentration of 100 μM of the particular peptide (duplicate determinations).

It is evident from FIG. 1 that short, soluble, tryptophan-containing, in particular tryptophan- and tyrosine-containing secretory peptides such as gonadotrophin releasing hormone (GnRH), and synthetic peptides, have antioxidant properties.

2.

In order to demonstrate that tryptophan, especially tryptophan and tyrosine, mediate the antioxidant effect of the secretory peptides, the behavior of modified or truncated peptides was investigated in the peroxy free radical trapping test described in example 1. The results are shown in FIG. 2. • means the control, ○ means a concentration of 200 nM, ▼ means a concentration of 2 μM and ∇ means a concentration of 20 μM of the particular peptide (quadruplicate determinations).

FIG. 2 also shows the antioxidant effect of truncated GnRH fragments. Whereas the effect occurring with GnRH 3-10 (WSYGLRPG-amide) (SEQ ID NO: 7) is similar to that with GnRH (cy-EHWSYGLRPG-amide), the antioxidant effect is markedly reduced with GnRH 4-10 (SYGLRPG-amide) (SEQ ID NO: 8), which lacks the tryptophan residue. A further truncation together with an absence of the tyrosine residue, as in GnRH 7-10 (LRPG-amide) (SEQ ID NO: 9), leads to a complete loss of activity.

3.

Experiments were carried out to test the antioxidant effect of other substances in the peroxy free radical trapping test described in example 1. The results are shown in FIG. 3 (see FIG. 1A for explanation). It was found from this that the peptides have a greater antioxidant effect than known antioxidants such as tocopherol and probucol and an effect which is at least comparable to that of melatonin and 17β-estradiol.

The invention claimed is:

1. A method for protecting a protein from oxidation comprising:
   (i) contacting said protein with a peptide which has a length of from 2 to 7 amino acids and contains an amino acid sequence selected from the group consisting of WY, WGY, WGGY (SEQ ID NO: 5), WGGGY (SEQ ID NO: 6), WW, and YY, or a peptide consisting of an amino acid sequence selected from the group consisting of SEQ ID NO: 1, SEQ ID NO: 2, SEQ ID NO: 3, SEQ ID NO: 4, SEQ ID NO: 7, or SEQ ID NO: 8,
   (ii) in an amount sufficient to protect said protein from oxidation.

2. The method as claimed in claim 1, wherein said peptide comprises at least one tryptophan residue and at least one tyrosine residue.

3. The method as claimed in claim 1, wherein said peptide comprises at least two tryptophan residues.

4. The method of claim 1, wherein said peptide has amphiphilic properties.

5. The method of claim 1, wherein said peptide has an appropriate, N- or/and C-terminal modification or a cyclic structure.

6. The method of claim 1, wherein said peptide comprises up to a total of four tyrosine residues.

7. The method of claim 1, wherein the peptide is selected from the group consisting of WY, WGY, WGGY (SEQ ID NO: 5), WGGGY (SEQ ID NO: 6), WW and YY.

8. The method of claim 1, wherein said protein is LDL or β-phycoerythrin.

9. The method of claim 1, wherein said peptide is selected from the group consisting of the peptide consisting of amino acid SEQ ID NO: 1, 2, 3, 4, 5, 6, 7, and 8.

10. The method of claim 9, wherein said protein is LDL or β-phycoerythrin.

* * * * *